US006362202B1

(12) United States Patent
Rubin et al.

(10) Patent No.: US 6,362,202 B1
(45) Date of Patent: Mar. 26, 2002

(54) METHODS AND COMPOSITIONS USING (−) NORCISAPRIDE IN COMBINATION WITH PROTON PUMP INHIBITORS OR $H_2$ RECEPTOR ANTAGONISTS

(75) Inventors: Paul D. Rubin, Sudbury; Timothy J. Barberich, Concord, both of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/507,951

(22) Filed: Feb. 22, 2000

Related U.S. Application Data
(60) Provisional application No. 60/122,393, filed on Mar. 2, 1999.

(51) Int. Cl.$^7$ .................... A61K 31/445; A61K 31/415; A61K 31/135
(52) U.S. Cl. ........................ 514/327; 514/393; 514/394; 514/653
(58) Field of Search ................................ 514/327, 393, 514/394, 653

(56) References Cited

U.S. PATENT DOCUMENTS

| | | | |
|---|---|---|---|
| 3,916,899 A | 11/1975 | Theeuwes et al. .......... | 128/260 |
| 4,008,719 A | 2/1977 | Theeuwes et al. .......... | 128/260 |
| 4,413,129 A | 11/1983 | Uchikuta et al. ........... | 548/342 |
| 4,544,750 A | 10/1985 | Brändström et al. ........ | 546/290 |
| 4,598,123 A | 7/1986 | Cutter .......................... | 525/84 |
| 4,620,008 A | 10/1986 | Brändström et al. ........ | 546/271 |
| 4,758,579 A | 7/1988 | Kohl et al. .................. | 514/338 |
| 4,855,439 A | 8/1989 | Zizek .......................... | 548/342 |
| 4,886,910 A | 12/1989 | Tan et al. .................... | 564/215 |
| 4,886,912 A | 12/1989 | Tan et al. .................... | 564/240 |
| 4,962,115 A | 10/1990 | Van Daele .................. | 514/326 |
| 5,045,552 A | 9/1991 | Souda et al. ................ | 514/338 |
| 5,057,427 A | 10/1991 | Wald et al. .................. | 435/280 |
| 5,057,525 A | 10/1991 | Van Daele .................. | 514/318 |
| 5,059,595 A | 10/1991 | Le Grazie ................... | 424/468 |
| 5,073,543 A | 12/1991 | Marshall et al. .............. | 514/21 |
| 5,077,217 A | 12/1991 | Matson et al. .............. | 435/280 |
| 5,118,813 A | 6/1992 | Reiner ......................... | 548/336 |
| 5,120,548 A | 6/1992 | McClelland et al. ........ | 424/473 |
| 5,137,896 A | 8/1992 | Van Daele .................. | 514/327 |
| 5,354,556 A | 10/1994 | Sparks et al. ............... | 424/419 |
| 5,374,730 A | 12/1994 | Slemon et al. .............. | 546/271 |
| 5,386,032 A | 1/1995 | Brëndström ................ | 546/271 |
| 5,470,983 A | 11/1995 | Slemon et al. .............. | 546/271 |
| 5,502,195 A | 3/1996 | Slemon et al. .............. | 546/271 |
| 5,541,335 A | 7/1996 | Manning .................... | 548/205 |
| 5,591,767 A | 1/1997 | Mohr et al. ................. | 514/413 |
| 5,639,476 A | 6/1997 | Oshlack et al. ............. | 424/468 |
| 5,663,173 A | 9/1997 | Jegham et al. .............. | 514/249 |
| 5,674,533 A | 10/1997 | Santus et al. ................ | 424/493 |
| 5,700,945 A | 12/1997 | Manning .................... | 548/208 |
| 5,712,293 A | 1/1998 | McCullough et al. ....... | 514/327 |
| 5,733,566 A | 3/1998 | Lewis ......................... | 424/426 |
| 5,739,151 A * | 4/1998 | McCullough et al. ....... | 514/327 |
| 5,877,189 A * | 3/1999 | MCullough et al. ........ | 514/327 |
| 6,156,770 A * | 12/2000 | McCullough et al. ....... | 514/327 |

FOREIGN PATENT DOCUMENTS

| | | |
|---|---|---|
| EP | 0 076 530 B1 | 4/1983 |
| EP | 0 364 274 A1 | 4/1990 |
| EP | 748 807 A1 | 12/1996 |
| WO | WO 93/12785 | 7/1983 |
| WO | WO 94/01111 | 1/1994 |
| WO | WO 94/01112 | 1/1994 |
| WO | WO 94/27599 | 12/1994 |
| WO | WO 95/01803 | 1/1995 |
| WO | WO 96/40133 | 12/1996 |
| WO | WO 98/03173 | 1/1998 |

OTHER PUBLICATIONS

Burks, T.F., Principles of Pharmacology, 1996, pp. 1093–1100.

Krejs, GJ "Sérotonine intestinale, une cible thérapeutique," Méd. Chir. Dig. 22:7:415–416 (1993).

Porsius, AJ et al., "Farmacotoets 6A," Farmacotherapie 129:9:214–217 (1994).

Barnes, N.M. et al., "Identification of 5–$HT_3$ Recognition Sites In The Ferret Area Postrema," J. Pharm. Pharmacol., 40:586–588 (1988).

Barone, Joseph A., et al., "Bioavailability of Three Oral Dosage Forms of Cisapride, A Gastrointestinal Stimulant Agent," Clinical Pharmacy 6:640–645 (1987).

Blecker, U. et al., "The Role of Occult Gastroesophageal Reflux in Chronic Pulmonary Disease in Children," Acta Gastro–Enterologica Belgica, 58(5–6):348–352 (1995).

Burks, T.F., "Drugs Affecting Gastrointestinal Motility and Antiemetic Agents" Principles of Pharmacology, 70:1093–1100 (1996).

Burstein, E.S. et al., "Structure–Function of Muscarinic Receptor Coupling to G Proteins," J. Biol. Chem., 270:3141–3146 (1995).

Brunton, L.L., "Agents for Control of Gastric Acidity and Treatment of Peptic Ulcers," Goodman & Gilman's The Pharmacological Basis of Therapeutics 9$^{th}$ Ed., 901–915 (1994).

(List continued on next page.)

Primary Examiner—Kevin E. Weddington
(74) Attorney, Agent, or Firm—Pennie & Edmonds, LLP

(57) ABSTRACT

The invention relates to methods and compositions for the prevention, treatment, or management of gastrointestinal disorders or symptoms thereof, employing two or more agents or compounds to provide a triple site action on 5-$HT_3$ receptors, 5-$HT_4$ receptors, and at least one of $H_2$ receptors and proton pumps.

23 Claims, No Drawings

OTHER PUBLICATIONS

Clarke, D. E. et al., "The 5–HT$_4$ Receptor: Naughty, But Nice," *Trends in Pharmacological Sciences*, 10:385–386 (1989).

Craig, D.A. et al., "5–Hydroxytryptamine and Cholinergic Mechanisms in Guinea–pig lleum," *Brit. J. Pharmacol.*, 96:247 (1989).

Costall, B., et al., "Emesis Induced By Cisplatin In The Ferret As A Model For The Detection Of Anti–Emetic Drugs," *Neuropharmacology*, 26:1321–1326 (1987).

Decktor, D.L., et al., "Effect of Metoclopramide, Bethanechol and the Cholecystokinin Receptor Antagonist, L–364, on Gastric Emptying in the Rat," *Eur. J. Pharmacol.*, 147:313–316 (1988).

Dumuis, A. et al., "The Gastrointestinal Prokinetic Benzamide Derivatives are agonists at the non–classical 5–HT receptor (5–HT$_4$) Positively Coupled To Adenylate Cyclase In Neurons," *N.S. Arch Pharmacol.*, 340:403–410 (1989).

Ebert, W.R., "Soft Elastic Gelatin Capsules: A Unique Dosage Form," *Pharm. Tech.*, 1(5):44–50 (1977).

Faris, P.L. et al., "Nociceptive, but not Tactile, Thresholds are Elevated in Bulimia Nervosa," *Biol. Psychiatry*32:462–466 (1992).

Fernandez, A.G., et al., "Peripheral Receptor Populations Involved in the Regulation of Gastrointestinal Motility and the Pharmacological Actions of Metoclopramide–like Drugs," *Life Sci.*, 36:1–14 (1985).

Frazer, A., et al., "Subtypes of Receptors for Serotonin," *Annual Rev. of Pharmacology and Toxicology*, 30:307–348 (1990).

Gladziwa, U., et al., "Pharmacokinetic and Pharmacodynamics of Cisapride in Patients Undergoing Hemodialysis," Pharmacol. 80(6) 673–681 (1991).

Guimaraens, D. et al., "Occupational Allergic Contact Dermatitis From Intermediate Products In Famotidine Synthesis," *Contact Dermatitis*, 31: 259–260 (1994).

Gullikson, G.W., et al., "Relationship of Serotonin–3 Receptor Antagonist Activity to Gastric Emptying and Motor–Stimulating Actions of Prokinetic Drugs in Dogs," *Journal of Pharmacology and Experimental Therapeutics*, 258(1):103–110 (1991).

Jamali, F., et al., "Enantioselective Aspects of Drug Action and Disposition: Therapeutic Pitfalls," *Journal of Pharmaceutical Sciences*, 78(9):605–715 (1989).

Lavrijsen, K., et al., "The Role of CYP3A4 in the In–Vitro Metabolism of Cisapride in Human Liver Microsomes and In–Vitro and In–Vivo Interactions of Cisapride with Co–Administered Drugs," Dept. of Pharmacokinetics and Drug Metabolism, Janssen Research Foundation 1995.

Lavrijsen, K., et al., "A Comparative Study on the In Vitro Metabolism of Cisapride Using Subcellar Liver Fractions of Dog, Rabbit, and Male and Female Rats", *Drug Development Research*, 8:267–278 (1986).

Lauwers, W., et al., "Identification of a Biliary Metabolite of Cisapride," *Biomedical and Environmental Mass Spectrometry*, 15:323–328 (1988).

Messier, T.L., et al., "High Throughput Assays of Cloned Adrenergic, Muscarinic, Neurokinin, and Neurotrophin Receptors in Living Mammalian Cells," *Pharmacol. Toxicol.*, 76(5):308–311 (1995).

Meuldermans, W. et al., "Excretion and Biotransformation of Cisapride In Dogs and Humans After Oral Administration," *Drug Metab. Dispos.*, 16(3):403–409 (1988).

Meuldermans, W. et al., "Excretion and Biotransformation of Cisapride in Rats After Oral Administration," *Drug. Metab. Dispos.*, 16(3):410–419(1988 ).

Milo, R., "Non–Cholinergic, Non–antidopaminergic Treatment of Chronic Digestive Symptoms Suggestive Of A Motility Disorder: A Two–Step Pilot Evaluation of Cisapride," *Curr. Therapeutic Research*, 36(5):1053–1062 (1984).

Nemeth, P.R., et al., "Gastrointestinal Motility Stimulating Drugs and 5–HT Receptors on Myenteric Neurons," *European Journal of Pharmacology*, 166:387–391 (1989).

Noor, N. et al., "Effects of Cisapride on Symptoms and Postcibal Small–Bowel Motor Function in Patients with Irritable Bowel Syndrome," *Scandinavian J. Gastroent.*, 33(6):605–611 (1998).

*Physician's Desk Reference*, 52Ed., 1308–1309 (1998).

Preechagoon, Y., et al., Analysis of Cisapride in Neonatal Plasma Using High–performance liquid chromatography with a Base–stable Column and Fluorescence Detection, *Journal of Chromatography B: Biomedical Applications*, 670:139–143 (1995).

Reyntjens, A., et al., "Clinical Pharmacological Evidence For Cisapride's Lack of Antidopaminergic or Direct Cholinergic Properties," *Current Therapeutic Research*, 36(5):1045–1052 (1984).

Schapira, M. et al., "The Current Status of Gastric Prokinetic Drugs," *Acta Gastroenterolog. Belg.*, 53:446–457 (1990).

Schiavi, G.B., et al., "Identification of Serotonin 5–HT$_4$ Recognition Sites in the Porcine Caudate Nucleus by Radioligand Binding," *Neuropharmacology*, 33:543–549 (1994).

Schuurkes, J.A.J., et al., "Motor–Stimulating Properties of Cisapride on Isolated Gastrointestinal Preparations of the Guinea Pig," *J. Pharmacol. Exp. Ther.*, 234:775–783 (1985).

Shah, M., "Gastroesophageal Reflux—How to Mend it?" *Indian J. Pediatr.*, 63:441–445 (1996).

Skinner, S., et al., "Gastric Under Presenting as Gastroesophageal Reflux and Apnea in a Term Neonate," *Tex. Medic.*, 94(9):57–58 (1998).

Stacher, G., et al., "Effects of Oral Cisapride on Interdigestive Jejunal Motor Activity, Psychomotor Function, and Side–Effect Profile in Healthy Man," *Digestive Disease and Sciences*, 32(11):1223–1230 (1987).

Van Daele, G.H. P. et al., "Synthesis of Cisapride, a Gastrointentestinal Stimulant Derived From Cis–4–Amino–3–Methoxypiperidine," *Drug Development Res.*, 8:225–232 (1986).

Vandenplas, Y., "Clinical Use of Cisapride and its Risk–benefit in Pediatric Patients," *Eur. J. Gastroent. Hepat.*, 10(10):871–881 (1998).

Van Peer, A. et al., "Clinical Pharmacokinetics of Cisapride," *Excerpta Medica, Current Clinical Practice Series*, A.G. Johnson and G. Lux, Eds. Amsterdam, 48:23–29 (1988).

Ward, R. M. et al., "Cisapride: A Survey of the Frequency of Use and Adverse Events in Premature Newbords," Pediatrics, 103(2):469–472 (1999).

Wong, R.H. et al., "The Antiemetic Effects of the R– and S–Enantiomers of Cisapride and Norcisapride Against Cisplatin–Induced Emesis in the Ferret" *Behavioral Pharmacology, Abstracts Society For Neuroscience 27th Annual Meeting Part 1* 23:415 (1997).

Williams, C.L. et al., "Cisapride Increases Gastric Emptying Without Affecting Small or Large Bowel Transit," *Proc. West. Pharmacol. Soc.*, 28:47–50 (1985).

Zuccato E., et al., "The Effects of S(–) and R(+) Sulpride, Metoclopramide, Cisapride and Domperidone on the Small Intestine Suggest $DA_2$–Receptors are Involved in the Control of Small Intestinal Transit Time In Rats," *Pharmacol. Rs.* 26(2);179–185 (1992).

* cited by examiner

METHODS AND COMPOSITIONS USING (−) NORCISAPRIDE IN COMBINATION WITH PROTON PUMP INHIBITORS OR $H_2$ RECEPTOR ANTAGONISTS

This application claim benefit to Provisional Application 60/122,393 Mar. 2, 1999.

FIELD OF THE INVENTION

The invention relates to methods and compositions for the prevention, treatment, or management of gastrointestinal disorders or symptoms thereof, by administering one or more agent(s) or compound(s) that simultaneously or sequentially act on a $5\text{-}HT_3$ receptor, a $5\text{-}HT_4$ receptor, and either an $H_2$ receptor or a proton pump.

BACKGROUND OF THE INVENTION

Gastrointestinal disorders are common disorders that affect the gastrointestinal tract, i.e., the stomach and intestines. Various gastrointestinal disorders exist, including: gastro-esophageal reflux disease, emesis, gastrointestinal motility dysfunction, gastrointestinal ulcers, pathological hypersecretory conditions, and gastric hyperacidity. These diseases may be treated by various non-invasive means, such as administering to a patient a therapeutic agent, such as ZANTAC® (ranitidine), TRITEC(® (ranitidine), AXID® (nizatidine), TAGAMET® (cimetidine), PREVACID® (lansoprazole), PEPCID®, PEPCID AC® ACID CONTROLLER™, MYLANTA AR ACID REDUCER™ (famotidine), PRILOSEC® (omeprazole), and others. New pharmaceutical compounds and preparations are continually being developed.

U.S. Pat. Nos. 4,962,115, 5,057,525, and 5,137,896 (collectively "Van Daele") disclose N-(3-hydroxy-4-piperidenyl)benzamides. These compounds are said to stimulate the motility of the gastrointestinal system. Van Deale states that the cis and trans diastereomeric racemates of these compounds may be obtained separately by conventional methods, and the cis and trans diastereomeric racemates may be further resolved into their optical isomers. One such racemate, Cisapride, is chemically named cis-4-amino-5-chloro-N-[1-[3-(4-fluorophenoxy)propyl]-3-methoxy-4-piperidinyl]-2-methoxybenzanide. Schapira et al., *Acta Gastroenterolog Belg.*, LIII:446–457 (1990). Cisapride is used primarily to treat gastroesophageal reflux disease ("GERD"), which is characterized as the backward flow of the stomach contents into the esophagus. Cisapride is commercially available as the racemic mixture of the cis(−) and cis(+) diastereomeric enantiomers of cisapride known as PROPULSID®.

Benzamide derivatives have several prominent pharmacological actions due to their effects on neuronal systems modulated by the neurotransmitter serotonin. It has been reported that a major site of production and storage of serotonin is the enterochromaffin cell of the gastrointestinal mucosa. It was also reported that serotonin provides a powerful intestinal transit and decreasing absorption time, as occurs with diarrhea. This stimulating action is also associated with nausea and vomiting.

Because of their modulation of the serotonin neuronal system in the gastrointestinal tract, some benzamide derivatives are effective antiemetic agents and are used to control vomiting during cancer chemotherapy or radiotherapy. Costall et al., *Neuropharmacology*, 26:1321–1326 (1987). This action is the result of an ability to block serotonin at specific sites, particularly Type-3 5-hydroxytryptamine ($5\text{-}HT_3$) receptors. Clarke et al., *Trends in Pharmacological Sciences*, 10:385–386 (1989). Chemotherapy and radiation therapy can induce nausea and vomiting by damaging enterochromaffin cells in the gastrointestinal tract. As a result, the neurotransmitter serotonin is released and stimulates both afferent vagal nerve fibers (thus initiating the vomiting reflex) and serotonin receptors in the chemoreceptor trigger zone of the area postrema region of the brain. The anatomical site for this action of the benzamide derivatives, and whether such action is central (CNS), peripheral, or a combination thereof, remains unresolved. Barnes et a., *J Pharm. Pharmacol.*, 40:586–588 (1988).

A second prominent action of certain benzamide derivatives is in augmenting gastrointestinal smooth muscle activity from the esophagus to the proximal small bowel, thus accelerating esophageal and small intestinal transit, as well as facilitating gastric emptying and increasing lower esophageal sphincter tone. Decktor et al., *Eur. J. Pharmacol.*, 147: 313–316 (1988). Although the benzamide derivatives are not cholinergic receptor agonists per se, the aforementioned smooth muscle effects may be blocked by muscarinic receptor blocking agents such as atropine or inhibitors of neuronal transmissions, such as the tetrodotoxin type that block sodium channels. Fernandez and Massingham, *Life Sci.*, 36: 1–14 (1985). Similar blocking activity has been reported for the contractile effects of serotonin in the small intestine. Craig and Clarke, *Brit. J. Pharmacol.*, 96: 247P (1989). It is believed that the primary smooth muscle effects of some benzamide derivatives are the result of an agonist action upon a class of serotonin receptors referred to as $5\text{-}HT_4$ receptors, which are located on intemeurons in the myenteric plexus of the gut wall. Clarke et al, *Trends in Pharmacological Sciences*, 10: 385–386 (1989) and Dumuis et al., *N. S. Arch. Pharmacol.*, 340: 403–410 (1989). Activation of these receptors subsequently enhances the release of acetylcholine from parasympathetic nerve terminals located near surrounding smooth muscle fibers. It is the combination of acetylcholine with its receptors on smooth muscle membranes which is the actual trigger for muscle contraction.

It has been reported that cisapride enters the central nervous system and binds to $5\text{-}HT_4$ receptors. This indicates that cisapride may have centrally-mediated effects. Cisapride is a potent ligand at $5\text{-}HT_4$ receptors, which are located in several areas of the central nervous system. Dumuis et al, *N.S. Arch. Pharmacol.*, 340: 403–410 (1989). Modulation of serotonergic systems may have a variety of behavioral effects.

The co-administration of racemic cisapride with other therapeutic agents causes inhibitory problems with the metabolism of cisapride by the liver. For example, ketoconazole has a pronounced effect on cisapride kinetics resulting from the inhibition of the metabolic elimination of cisapride and leads to an 8-fold increase of the steady-state plasma levels. *Physician's Desk Reference®*, Medical Economics Co., Inc., p. 1308–1309, $52^{nd}$ Edition (1998). Interaction of racemic cisapride and other therapeutic agents can also potentiate cardiovascular side effects, such as cardiotoxicity. This potentiation occurs when other drugs present in the patient's system interfere with the metabolism of cisapride, thereby causing a build up of racemic cisapride in the body.

These interactions are a significant drawback to the use of racemic cisapride; in particular, because racemic cisapride is often used before, with, or immediately after another therapeutic agent. In addition, administration of racemic cisapride to a human has been found to cause adverse effects such as cardiac arrhythmia, including ventricular tachycardia, ventricular fibrillation, $Q_T$ prolongation, and torsades de pointes, central nervous system ("CNS") effects, increased systolic pressure, interactions with other drugs, diarrhea, abdominal cramping, and cardiac depression.

Racemic cisapride in humans is metabolized mainly by oxidative N-dealkylation of the piperidine nitrogen or by aromatic hydroxylation occurring on either the 4-fluorophenoxy or benzamide rings. Meuldermans et al., *Drug Metab. Dispos.*, 16(3):410–419 (1988); and Meuldermans et al., *Drug Metab. Dispos.*, 16(3):403–409 (1988). Norcisapride, chemically named 4-amino-5-chloro-N-(3-methoxy-4-piperidinyl)-2-methoxybenzamide, is an active metabolite of cisapride.

Recently, investigators have reported that the optically pure (−) stereoisomer of the cisapride metabolite norcisapride exhibits many useful characteristics, but without certain side effects of racemic cisapride. Specifically, U.S. Pat. No. 5,712,293 discloses a method of treating gastroesophageal reflux disease and other conditions, including emesis, dyspepsia, constipation, gastroparesis, intestinal pseudo obstruction, and post-operative ileus using optically pure (−) norcisapride.

Other agents or compounds which have been studied for the treatment of gastrointestinal diseases include proton pump inhibitors and $H_2$ receptor antagonists. Proton pump inhibitors treat gastrointestinal diseases by inhibiting $H^+$-$K^+$ ATPase and thereby regulating acidity in gastric juices. $H_2$ receptor antagonists inhibit histamine binding with $H_2$ receptors to regulate gastric acid secretion. Goodman & Gilman, *The Pharmacological Basis of Therapeutics*, 9$^{th}$ Edition, pp. 901–915 (1996).

The concentration gradients of gastric acids across cell membranes vary widely. Perhaps the largest gradient in the body occurs across the plasma membrane of the parietal cells of the stomach lining, which secrete hydrochloric acid into gastric juice. Since the concentration of hydrochloric acid in gastric juice may be as high as 0.1 M and the concentration of $H^+$ in the cells is about $10^{-7}$ M, parietal cells can secrete $H^+$ions against a concentration gradient of about 1 million to 1. A membrane-bound enzyme called $H^+$-$K^+$ ATPase facilitates active transport of $H^+$across membranes against concentration gradients in exchange for $K^+$ to form gastric hydrochloric acid. For each molecule of cytosolic ATP hydrolyzed to ADP and phosphate, 2 $H^+$ ions are transported across the plasma membrane from the cytosol to the stomach. Goodman & Gilman, *The Pharmacological Basis of Therapeutics*, 9$^{th}$ Edition, pp. 901–915 (1996).

Proton pump inhibitors suppress gastric acid secretion, the final step of acid production, by specific inhibition of the $H^+$-$K^+$ ATPase enzyme system at the secretory surface of gastric parietal cells. Proton pump inhibitors include benzimidazole compounds, for example, omeprazole (PRILOSEC®), lansoprazole (PREVACIDS®), and pantoprazole. These proton pump inhibitors contain a sulfinyl group situated between substituted benzimidazole and pyridine rings. At neutral pH, omeprazole, lansoprazole, and pantoprazole are chemically stable, lipid soluble, weak bases that are devoid of inhibitory activity. These uncharged weak bases reach parietal cells from the blood and diffuse into the secretory canaliculi, where the drugs become protonated and thereby trapped. The protonated species rearranges to form a sulfenic acid and a sulfenamide, the latter species capable of interacting with sulfhydryl groups of $H^+$-$K^+$ ATPase. Full inhibition occurs with two molecules of inhibitor per molecule of enzyme. The specificity of the effects of proton pump inhibitors is believed to derive from: a) the selective distribution of $H^+$-$K^+$ ATPase; b) the requirement for acidic conditions to catalyze generation of the reactive inhibitor; and c) the trapping of the protonated drug and the cationic sulfenamide within the acidic canuliculi and adjacent to the target enzyme. Goodman & Gilman's *The Pharmacological Basis of Therapeutics*, 9$^{th}$ Edition, pp. 901–915 (1996).

$H_2$ receptor antagonists competitively inhibit the interaction of histamine with $H_2$ receptors. They are highly selective and have little or no effect on $H_1$ receptors. Although $H_2$ receptors are present in numerous tissues, including vascular and bronchial smooth muscle, $H_2$ receptor antagonists interfere remarkably little with physiological functions other than gastric acid secretion. $H_2$ receptor antagonists include nizatidine (AXID®), ranitidine (ZANTAC® and TRITEC®), famotidine (PEPCID AC®), and cimetidine (TAGAMET®). Goodman & Gilman's *The Pharmacological Basis of Therapeutics*, 9$^{th}$ Edition, pp. 901–915 (1996).

$H_2$ receptor antagonists inhibit gastric acid secretion elicited by histamine, other $H_2$ agonists, gastrin, and, to a lesser extent, muscarinic agonists. $H_2$ receptor antagonists also inhibit basal and nocturnal acid secretion, and this effect contributes in a major way to their clinical efficacy.

Although therapeutic agents are available, there remains a need for a more effective, broad-spectrum treatment or therapy for gastrointestinal disorders. For example, it is desirable to have safe and effective methods and compositions for preventing, treating, and managing gastrointestinal disorders without adverse effects or adverse drug-drug interactions.

SUMMARY OF THE INVENTION

The invention encompasses the prevention, treatment, or management of gastrointestinal disorders by biological action at three different sites: action at 5-$HT_3$ receptors, 5-$HT_4$ receptors, and either $H_2$ receptors or proton pumps. The use of triple action is considered to provide an unexpectedly superior therapeutic profile. The use of this triple action therapy can be less toxic and/or more potent for preventing, treating, and managing gastrointestinal disorders than the use of agents that act on any of the three sites alone.

In one embodiment, three therapeutic agents or compounds are used, one providing action at 5-$HT_3$ receptors, another providing action at 5-$HT_4$ receptors, and the third being either a proton pump inhibitor or an $H_2$ receptor antagonist. For example, in a preferred embodiment, cisapride, ondansetron, and either a proton pump inhibitor or an $H_2$ receptor antagonist are used to prevent, treat, or manage gastrointestinal disorders. In a more preferred embodiment, either optically pure (+) cisapride or optically pure (−) cisapride, or a pharmaceutically acceptable salt thereof, optically pure R(+) ondansetron, or a pharmaceutically acceptable salt thereof, and either a proton pump inhibitor or an $H_2$ receptor antagonist are used.

In another embodiment, the invention encompasses the synergistic use of two or more agents or compounds to provide triple site action on 5-$HT_3$ receptors, 5-$HT_4$ receptors, and either $H_2$ receptors or proton pumps. In a preferred embodiment, two agents or compounds are used, one providing dual action at 5-$HT_3$ receptors and 5-$HT_4$ receptors, and another providing action either at $H_2$ receptors or proton pumps. For example, in this preferred embodiment, optically pure (−) norcisapride, or a pharmaceutically acceptable salt thereof, which has both 5-$HT_3$ and 5-$HT_4$ activity, and either a proton pump inhibitor or $H_2$ receptor antagonist are used to prevent, treat, or manage gastrointestinal disorders.

This invention also encompasses the use of two separate pharmaceutical compositions adapted for the prevention, treatment, or management of a patient suffering from gastrointestinal disorders or symptoms thereof, one which comprises a therapeutically effective amount of optically pure (−) norcisapride, or a pharmaceutically acceptable salt thereof, and another which a therapeutically effective amount of either a proton pump inhibitor or $H_2$ receptor antagonist.

Alternatively, the invention also encompasses pharmaceutical compositions comprising optically pure (−) norcisapride, or a pharmaceutically acceptable salt thereof, in combination with a either a proton pump inhibitor or an $H_2$ receptor antagonist. Such single unit dosage forms comprise from about 0.5 mg to about 500 mg of optically pure (−) norcisapride, or a pharmaceutically acceptable salt thereof, and from about 1 mg to about 200 mg of a proton pump inhibitor or from about 1 mg to about 2400 mg an $H_2$ receptor antagonist, in a suitable carrier.

The pharmaceutical compositions and methods of the invention, particularly those which comprise a therapeutically effective amount of optically pure (−) norcisapride, or a pharmaceutically acceptable salt thereof, can be used to prevent or alleviate symptoms of gastrointestinal disorders, while reducing or avoiding adverse effects associated with administration of conventional treatments such as conventional 5-$HT_3$ receptor antagonists, 5-$HT_4$ receptor agonists or antagonists, $H_2$ receptor antagonists, and proton pump inhibitors. Moreover, the compositions and methods of the present invention encompass the treatment, prevention or management of gastrointestinal disorders while reducing or avoiding adverse drug-drug interactions which are known to occur with the use of existing commercial agents, such as racemic cisapride.

DETAILED DESCRIPTION OF THE INVENTION

The invention encompasses the prevention, treatment, or management of gastrointestinal disorders by biological action at three different sites, action on 5-$HT_3$ receptors, 5-$HT_4$ receptors, and either $H_2$ receptors or proton pumps (e.g., inhibition of $H^+$-$K^+$-ATPase enzyme system). The use of triple-site action is considered to provide an unexpectedly superior therapeutic profile to conventional treatment of gastrointestinal disorders. The use of this triple action therapy can be safer and/or more effective for preventing, treating, and managing gastrointestinal disorders than the use of agents that act on any of the three sites alone.

More specifically, the invention also encompasses the use of at least three agents or compounds to prevent, treat, or manage gastrointestinal disorders, or symptoms thereof, one providing action at 5-$HT_3$ receptors, another providing action at 5-$HT_4$ receptors, and a third providing action at either proton pump systems or $H_2$ receptors. Preferably, the three compounds are cisapride, ondansetron, and either a proton pump inhibitor or an $H_2$ receptor antagonist. More preferably, the three compounds are either optically pure (+) cisapride or optically pure (−) cisapride, or a pharmaceutically acceptable salt thereof, optically pure R(+) ondansetron or a pharmaceutically acceptable salt thereof, and either a proton pump inhibitor or $H_2$ receptor antagonist.

The invention also encompasses the synergistic use of at least two agents or compounds to provide triple action on 5-$HT_3$ receptors, 5-$HT_4$ receptors, and either $H_2$ receptors or the proton pump mechanism in the prevention, treatment, or management of gastrointestinal disorders. Preferably, two agents or compounds are used, one providing dual action at 5-$HT_3$ receptors and 5-$HT_4$ receptors, and another providing action at either $H_2$ receptors or proton pump systems. More preferably, the two agents or compounds are optically pure (−) norcisapride, or a pharmaceutically acceptable salt thereof, and either an $H_2$ receptor antagonist or a proton pump inhibitor.

Gastrointestinal disorders that can be treated by the compositions and methods of the invention include, but are not limited to, disorders of the upper and lower gastrointestinal system, gastro-esophageal reflux disease ("GERD"), emesis, gastrointestinal motility dysfunction, gastrointestinal ulcers, pathological hypersecretory conditions, and gastric hyperacidity. The gastrointestinal disorders additionally include, but are not limited to, dyspepsia, gastroparesis, constipation, post-operative ileus, intestinal pseudo obstruction, gastric ulcers, duodenal ulcers, heartburn, acid indigestion, erosive esophagitis, sour stomach, upset stomach and Zollinger-Ellison Syndrome.

In a most preferred embodiment, the invention encompasses the use of the optically pure (−) norcisapride, or a pharmaceutically acceptable salt thereof, and at least one of a proton pump inhibitor or an $H_2$ receptor antagonist, in preventing, treating, or managing gastrointestinal disorders, or symptoms thereof. It should be noted that racemic norcisapride, or a pharmaceutically acceptable salt thereof, may be used as an alternative to optically pure (−) norcisapride in the methods and compositions of the invention, although optically pure (−) norcisapride is preferred. Similarly, optically pure stereoisomers or active metabolites of the proton pump inhibitors or the $H_2$ antagonists may also be use as alternatives where appropriate, as well as pharmaceutically acceptable salts thereof. Specific examples by way of illustration only are set forth herein.

Without being limited by theory, it is believed that utilization of an agent or compound having dual activity as a 5-$HT_3$ receptor antagonist and a 5-$HT_4$ receptor agonist along with either a proton pump inhibitor or an $H_2$ receptor antagonist provides triple-site action, which surprisingly results in clearer dose-related definitions of efficacy, diminished adverse effects, a superior therapy due to synergistic activity, and accordingly, an improved therapeutic index. For example, optically pure (−) norcisapride has dual activity as a 5-$HT_3$ receptor antagonist and a 5-$HT_4$ receptor agonist, and triple-site action is achieved when used with either a proton pump inhibitor or an $H_2$ receptor antagonist. It is, therefore, more desirable to use the compositions and methods of the invention than to use a 5-$HT_3$ receptor antagonist, a 5-$HT_4$ receptor agonist, an agent or compound having dual activity as a 5-$HT_3$ receptor antagonist and a 5-$HT_4$ receptor agonist, a proton pump inhibitor, or an $H_2$ receptor antagonist alone.

The use of the optically pure (−) norcisapride, or a pharmaceutically acceptable salt thereof, with either a proton pump inhibitor or an $H_2$ receptor antagonist, in preventing, treating, or managing gastrointestinal disorders, in accordance with the present invention is consider to reduce or avoid adverse effects associated with existing commercial treatment for gastrointestinal disorders, such as racemic cisapride. Further, this embodiment is considered to reduce or avoid adverse drug-drug interactions associated with racemic cisapride.

The invention also encompasses methods of preventing, treating, or managing a condition caused by a dysfunction of 5-$HT_3$ receptors, 5-$HT_4$ receptors, or proton pumps or $H_2$ receptors by administering a therapeutically effective amount of optically pure (−) norcisapride, or a pharmaceutically acceptable salt thereof, with a therapeutically effective amount of either a proton pump inhibitor or an H$_2$ receptor antagonist.

The invention encompasses methods of preventing, treating, or managing GERD, emesis, gastrointestinal motility dysfinction, gastrointestinal ulcers, pathological hypersecretory conditions, or gastric hyperacidity which comprise administering to a patient a therapeutically effective amount of optically pure (−) norcisapride, or a pharmaceutically acceptable salt thereof, with either a proton pump inhibitor or an H$_2$ receptor antagonist. In specific embodiments, the invention also encompasses the use of these agents in combination for preventing, treating, or managing erosive esophagitis, dyspepsia, gastroparesis, constipation, post-operative ileus, intestinal pseudo obstruction, gastric ulcers, duodenal ulcers, heartburn, acid indigestion, erosive esophagitis, sour stomach, upset stomach, and Zollinger-Ellison Syndrome.

The invention, which encompasses the use of triple action therapy, may optionally further include the use of one or more additional therapeutic agents known to treat gastrointestinal disorders. Examples of such additional therapeutic agents include, but are not limited to, hydroxyzine (ANTARAX®); diphenhydramine (BENADRYL PARENTAREL®); prochlorperazine (COMPAZINE®); dronabinol (MARINOL®); promethazine (PHENERGAN®); meclizine (ANTIVERT®); trimethobenzamide (TIGAN®); thiethylperazine (TORECAN®); perphenazine (TRILAFON®); sucralfate (CARAFATE®); and the like, and where applicable, optically pure stereoisomers or active metabolites thereof.

The administration of two or more therapeutic agents used in accordance with the methods of the invention may be concurrent, sequential, or both, i.e., optically pure (−) norcisapride, or a pharmaceutically acceptable salt thereof, and either a proton pump inhibitor or an H$_2$ receptor antagonist, and optionally an additional therapeutic agent, may be administered as a combination, concurrently but separately, or by sequential administration.

The methods and compositions of this invention are considered to provide the benefit of reducing or avoiding adverse effects associated with prior methods and compositions used in the treatment of gastrointestinal disorders. See, e.g., *Physician's Desk Reference®*, Medical Economics Co., Inc., 52$^{nd}$ Edition (1998 and 1999).

The terms "adverse effects" and "adverse side effects," as used herein, include, but are not limited to, cardiac arrhythmia, cardiac conduction disturbances, appetite stimulation, weight gain, sedation, gastrointestinal distress, headache, dry mouth, constipation, diarrhea, and drug-drug interactions. The term "cardiac arrhythmia" includes, but is not limited to, ventricular tachyrhythmia, torsades de pointes, Q$_T$ prolongation, and ventricular fibrillation.

The term "gastrointestinal disorder," as used herein, includes, but is not limited to, gastrointestinal motility dysfimction, GERD, emesis, gastrointestinal ulcers, pathological hypersecretory conditions, gastric hyperacidity, erosive esophagitis, dyspepsia, gastroparesis, constipation, post-operative ileus, intestinal pseudo obstruction, gastric ulcers, duodenal ulcers, heartburn, acid indigestion, erosive esophagitis, sour stomach, upset stomach, and Zollinger-Ellison Syndrome.

The term "patient," as used herein, refers to a mammal, particularly a human.

The term "racemic," as used herein, is defined as a mixture of the (−) and (+) enantiomers of a compound wherein the (−) and (+) enantiomers are present in approximately a 1:1 ratio.

The phrase "optically pure," as used herein, means that the composition contains greater than about 90% of the desired stereoisomer by weight, preferably greater than about 95% of the desired stereoisomer by weight, and more preferably greater than about 99% of the desired stereoisomer by weight, based upon the total weight of the active ingredient, e.g., norcisapride when used to qualify (−) norcisapride. The term "substantially free," as used herein, means less than about 10 weight percent, preferably less than about 5 weight percent, and more preferably less than about 1 weight percent of the undesired stereoisomer, e.g., (+) norcisapride, is present according to the invention.

The phrase "5-HT$_3$ receptor antagonist," as used herein, means a compound capable of binding reversibly to a Type-3 5-hydroxytryptamine receptor. 5-HT$_3$ receptor antagonists include, but are not limited to, granisetron (KYTRIL®), metoclopramide (REGLAN®), ondansetron (ZOFRAN®), renzapride, zacopride, tropisetron, and where applicable, optically pure stereoisomers or active metabolites thereof.

The phrase "5-HT$_4$ receptor agonist," as used herein, means a compound capable of binding reversibly to a Type-4 5-hydroxytryptamine receptor. 5-HT$_4$ receptor agonists include, but are not limited to, norcisapride and cisapride, and where applicable, optically pure stereoisomers or active metabolites thereof The phrase "proton pump," as used herein, refers to H$^+$-K$^+$ ATPase, a membrane-bound enzyme that facilitates active transport of H$^+$across membranes against a concentration gradient.

The phrase "proton pump inhibitor," as used herein, refers to any agent or compound that inhibits or suppresses gastric acid secretion by inhibition of the H$^+$-K$^+$ ATPase enzyme system at the secretory surface of gastric parietal cells. Proton pump inhibitors include, but are not limited to, prazole derivatives, such as omeprazole lansoprazole, pantoprazole, rabeprazole, and where applicable, optically pure stereoisomers such as optically pure (+) lansoprazole, optically pure (−) lansoprazole, optically pure (+) omeprazole, optically pure (−) omeprazole, optically pure (+) rabeprazole, optically pure (−) rabeprazole, optically pure (+) pantoprazole and optically pure (−) pantoprazole, or active metabolites thereof. Active metabolites of proton pump inhibitors suitable for use according to the invention include, but are not limited to, hydroxy-omeprazole, hydroxy-lansoprazole, the carboxylic acid derivative of omeprazole, and desmethyl-pantoprazole, and where applicable, optically pure stereoisomers thereof. Omeprazole, lansoprazole, pantoprazole, and rabeprazole, for example, may be prepared by syntheses known to those of ordinary skill in the art, particularly from U.S. Pat. Nos. 4,544,750, 4,620,008, 4,620,008, 4,758,579, 5,045,552, 5,374,730, 5,386,032, 5,470,983, and 5,502,195, the disclosures of which are each incorporated herein by express reference thereto.

The phrase "H$_2$ receptor antagonist," as used herein, refers to any agent or compound that competitively inhibits the interaction of histamine with H$_2$ receptors. H$_2$ receptor antagonists include, but are not limited to, cimetidine, famotidine, ranitidine, nizatidine, and where applicable, optically pure stereoisomers or active metabolites thereof. Active metabolites of H$_2$ receptor antagonists include, but are not limited to, N2-monodesmethylnizatidine and where applicable, optically active stereoisomers thereof Nizatidine may be prepared by synthesis known to those of ordinary skill in the art, particularly from U.S. Pat. Nos.

5,541,335 and 5,700,945, the disclosures of which are each incorporated herein by express reference thereto. Ranitidine may be prepared by synthesis known to those of ordinary skill in the art, particularly from U.S. Pat. No. 5,118,813, the disclosure of which is each incorporated herein by express reference thereto. Cimetidine may be prepared by synthesis known to those of ordinary skill in the art, particularly from U.S. Pat. Nos. 4,413,129, 4,855,439, 4,886,910, 4,886,912, and 5,118,813, the disclosures of which are each incorporated herein by express reference thereto. Moreover, famotidine may be prepared by synthesis known to those of ordinary skill in the art, described in, for example, Guimaraens et al., *Contact Dermatitis,* 31(4):259 (1994).

The diseases prevented, treated, or managed in the invention are herein used consistently according to *Stedman's Medical Dictionary,* 26th Edition, Williams and Wilkins (1995).

The terms "gastro-esophageal reflux disease" or "GERD," as used herein, is defined as a condition characterized by the backward flow of the stomach contents into the esophagus.

The term "gastrointestinal ulcer," as used herein, is defined as a condition characterized by a lesion or lesions on the surface of the lining of the gastrointestinal tract, caused by superficial loss of tissue, usually accompanied by inflammation. Gastrointestinal ulcers include, but are not limited to, duodenal ulcers, and gastric ulcers.

The phrase "erosive esophagitis," as used herein, is defined as a condition characterized by inflammation of the lower esophagus from regurgitation of acid gastric contents, usually due to malfunction of the lower esophogeal sphincter.

The term "dyspepsia," as used herein, is defined as a condition characterized by an impairment of the power or function of digestion that can arise as a symptom of primary gastrointestinal dysfunction or as a complication due to other disorders, such as appendicitis, gallbladder disturbances, or malnutrition.

The term "gastroparesis," as used herein, is defined as a paralysis of the stomach brought about by a motor abnormality in the stomach or as a complication of diseases, such as diabetes, progressive systemic sclerosis, anorexia nervosa, or myotonic dystrophy.

The term "constipation," as used herein, is defined as a condition characterized by infrequent or difficult evacuation of feces resulting from conditions, such as lack of intestinal muscle tone or intestinal spasticity.

The phrase "post-operative ileus," as used herein, is defined as an obstruction in the intestine due to a disruption in muscle tone following surgery.

The terms "preventing" and "prevention," as used herein, are defined respectively as to stop or hinder and the act of stopping or hindering conditions or disorders in a patient who is at risk of suffering from such conditions or disorders, including, but not limited to, patients who suffer from stress.

The phrase "intestinal pseudo-obstruction," as used herein, is defined as a condition characterized by constipation, colicky pain, and vomiting, but without evidence of physical obstruction.

The phrase "gastric hyperacidity," as used herein, is defined as a condition characterized by an abnormally high degree of acidity in the gastric juices.

The phrase "therapeutically effective amount," as used herein, is defined as that amount of a therapeutic agent, which, alone or in combination with other drugs, provides a therapeutic benefit in the prevention, treatment, or management of gastrointestinal disorders, but not limited to, gastrointestinal motility dysfimction, GERD, emesis, gastrointestinal ulcers, pathological hypersecretory conditions, gastric hyperacidity, or symptoms thereof. Different therapeutically effective amounts may be applicable for each disorder, as will be readily known by those of ordinary skill in the art.

Optically pure (−) norcisapride may be obtained from a racemic mixture of cisapride, the chemical synthesis of which can be performed according to the method described in European Patent Application No. 0,076,530 A2 published Apr. 13, 1983, or U.S. Pat. Nos. 4,962,115, 5,057,525 or 5,137,896, the disclosures of which are each incorporated herein by express reference thereto. See also, Van Daele, et al., *Drug Development Res.,* 8:225–232 (1986). The metabolism of cisapride to norcisapride is described in Meuldermans, W., et al., *Drug Metab. Dispos.,* 16(3): 410–419 (1988) and Meuldermans, W., et al., *Drug Metab. Dispos.,* 16(3):403–409 (1988). The preparation of racemic norcisapride is also known to those of ordinary skill in the art, particularly in view of EP 0,076,530 A2 and U.S. Pat. No. 5,137,896 to Van Daele, the disclosures of which are each incorporated herein by express reference thereto. Optically pure stereoisomers of the chiral compounds discussed herein may also be obtained from the racemic mixture by resolution of the enantiomers using conventional means, for example, from an optically active resolving acid. The resolution of racemic compounds is also known to those of ordinary skill in the art, particularly from Jacques, J., et al., *Enantiomers, Racemates and Resolutions,* Wiley-Interscience, New York (1981); Wilen, S. H., et al., *Tetrahedron,* 33:2725 (1977); Eliel, E. L. *Stereochemistry of Carbon Compounds,* McGraw-Hill, N.Y., (1962); Wilen, S. H. *Tables of Resolving Agents and Optical Resolutions,* E. L. Eliel, Ed., Univ. of Notre Dame Press, Notre Dame, Ind., p. 268 (1972).

In addition to separation techniques, such as those described above, optically pure compounds may be synthesized by stereospecific synthesis using methodology well known to those of ordinary skill in the art. Chiral synthesis can result in products of high enantiomeric purity. However, in some cases, the enantiomeric purity of the product is not sufficiently high. The skilled artisan will appreciate that the separation methods described above may be used to further enhance the enantiomeric purity of the active stereoisomers which are obtained by chiral synthesis.

For example, optically pure (−) norcisapride may also be prepared from the racemic norcisapride mixture by enzymatic biocatalytic resolution. This synthesis is known to those of ordinary skill in the art, particularly from U.S. Pat. Nos. 5,057,427 and 5,077,217, the disclosures of which are each incorporated herein by express reference thereto.

The magnitude of a prophylactic or therapeutic dose of the active ingredients discussed herein, e.g., (−) norcisapride, a $5\text{-HT}_3$ antagonist, a $5\text{-HT}_4$ agonist or antagonist, a proton pump inhibitor, or an $H_2$ receptor antagonist, in the acute or chronic management of diseases and disorders described herein, will vary with the nature and severity of the condition to be prevented, treated, or managed and the route of administration. For example, oral, mucosal (including rectal), parenteral (including subcutaneous, intramuscular, bolus injection, and intravenous), sublingual, transdermal, nasal, buccal, and like may be employed. Dosage forms include tablets, caplets, troches, lozenges, dispersions, suspensions, suppositories, solutions, capsules, soft elastic gelatin capsules, patches, and the like. The dose, and perhaps the dose frequency, will also vary according to the age, body weight, and response of the individual patient. Suitable dosing regimens can be readily selected by those skilled in the art with due consideration of such factors.

In general, the total daily dosage of a 5-$HT_3$ receptor antagonist, a 5-$HT_4$ receptor agonist, or a therapeutic agent providing dual action at 5-$HT_3$ receptors and 5-$HT_4$ receptors for the conditions described herein, is from about 0.5 mg to about 500 mg, preferably from about 1 mg to about 350 mg, and more preferably from about 2 mg to about 250.

Suitable daily dosage ranges of proton pump inhibitors can be readily determined by those skilled in the art. In general the total daily dosage of a proton pump inhibitor for the conditions described herein, such as lansoprazole, pantoprazole, rabeprazole, omeprazole, or optically pure stereoisomers or active metabolites thereof, is from about 1 mg to about 200 mg, preferably from about 5 mg to about 150 mg, and more preferably from about 10 mg to about 100 mg.

In addition, suitable daily dosage ranges of $H_2$ receptor antagonists can be readily determined by those skilled in the art. For example, see the *Physician's Desk Reference®*, Medical Economics Co., Inc., $52^{nd}$ Edition (1999) for suitable dosages presently used for known $H_2$ receptor antagonists. For example, ranitidine may be administered using an oral daily dose range from about 1 mg to about 800 mg, preferably from about 100 mg to about 600 mg, and more preferably from about 250 mg to about 500 mg. For cimetidine, the oral daily dose range may be from about 1 mg to about 2400 mg, preferably from about 400 mg to about 1600 mg, more preferably from about 600 mg to about 1000 mg. For famotidine, the oral daily dose range may be from about 1 mg to about 200 mg, preferably from about 10 mg to about 80 mg, more preferably from about 15 mg to about 50 mg. For nizatidine, the oral daily dose range may be from about 1 mg to about 600 mg, preferably from about 50 mg to about 500 mg, more preferably from about 250 mg to about 350 mg.

In managing the patient, the therapy may be initiated at a lower dose, e.g., from about 0.5 mg to about 10 mg of (−) norcisapride and from about 1 mg to about 5 mg of a proton pump inhibitor or from about 1 mg to about 5 mg of an $H_2$ receptor antagonist, and increased up to the recommended daily dose or higher depending on the patient's global response. It is further recommended that children, patients over 65 years, and those with impaired renal or hepatic function, initially receive low doses, and that they be titrated based on individual response(s) and blood level(s). It may be necessary to use dosages of each active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Pharmaceutical compositions for use in the present invention can comprise a 5-$HT_3$ receptor antagonist and 5-$HT_4$ receptors agonist, or a therapeutic agent providing dual action at 5-$HT_3$ receptors and 5-$HT_4$ receptors with either a proton pump inhibitor or $H_2$ receptor antagonist as the active ingredients, and may additionally contain a pharmaceutically acceptable carrier, and optionally, other therapeutic ingredients.

In one embodiment, the pharmaceutical compositions comprise three therapeutic agents, a 5-$HT_3$ receptor antagonist and a 5-$HT_4$ receptor agonist with a proton pump inhibitor or $H_2$ receptor antagonist, and may additionally contain a pharmaceutically acceptable carrier, and optionally, other therapeutic ingredients. In a preferred embodiment, the pharmaceutical compositions comprise two therapeutic agents, one providing dual action at 5-$HT_3$ receptors and 5-$HT_4$ receptors, and the other is either a proton pump inhibitor or $H_2$ receptor antagonist.

As used herein, the term "pharmaceutically acceptable salt" refers to a salt prepared from pharmaceutically acceptable non-toxic acids including, but not limited to inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, benzoic camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, alginic, galacturonic, and the like. Particularly preferred acids are hydrobromic, hydrochloric, phosphoric, and sulfuric acids. In one embodiment, a 5-$HT_3$ receptor antagonist, a 5-$HT_4$ receptor agonist, or a therapeutic agent providing dual action as a 5-$HT_3$ receptor antagonist and a 5-$HT_4$ receptor agonist are administered as the free base or hydrate. For example, optically pure (−) norcisapride is administered as a free base or hydrate.

The invention also contemplates the use of active agents or compounds that are acidic, in which salts may be prepared from pharmaceutically acceptable non-toxic bases including organic, inorganic bases, solvates, hydrates, or clathrates thereof. Such inorganic bases include, but are not limited to, metallic salts of aluminum, calcium, lithium, magnesium, potassium, sodium, and zinc. Appropriate organic bases include, but are not limited to, N,N-dibenzylethylenediamine, chloroprocaine, choline, diethanolamine, ethylenediamine, meglumaine (N-methylglucamine), lysine, and procaine.

In practical use, the active agents in the pharmaceutical compositions of the invention can be combined as the active ingredients in intimate admixture with a pharmaceutically acceptable carrier according to conventional pharmaceutical compounding techniques. The carrier may take a wide variety of forms and comprises a number of components depending on the form of preparation desired for administration. The compositions of the present invention include, but are not limited to, suspensions, solutions and elixirs; aerosols; or excipients, including, but not limited to, starches; sugars, microcrystalline cellulose, diluents, granulating agents, lubricants, binders, disintegrating agents, and the like. Preferably, the pharmaceutical composition is in the form of an oral preparation. Because of their ease of administration, tablets and capsules are preferred and represent the most advantageous oral dosage unit form, in which case solid pharmaceutical excipients are employed. If desired, tablets may be coated by standard aqueous or nonaqueous techniques.

Preferably, the oral pharmaceutical compositions of the present invention may be administered in single or divided doses, from one to four times a day. The oral dosage forms may be conveniently presented in unit dosage forms and prepared by any methods well known in the art of pharmacy.

Pharmaceutical compositions of the present invention suitable for oral administration may be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Such compositions may be prepared by any methods well known in the art of pharmacy, but all methods include the step of bringing into association one or more active ingredient(s) with the carrier. In general, the compositions are prepared by uniformly and intimately admixing the active ingredients with liquid carriers or finely divided solid carriers or both, and then, if necessary, shaping the product into the desired presentation. Oral solid preparations are preferred over oral liquid preparations. One preferred oral solid preparation is capsules, but the most preferred oral solid preparation is tablets.

For example, a tablet may be prepared by compression or molding, optionally, with one or more accessory ingredients. Compressed tablets may be prepared by compressing in a suitable machine the active ingredient in a free-flowing form, such as powder or granules, optionally mixed with a binder, lubricant, inert diluent, granulating agent, surface active or dispersing agent, or the like. Molded tablets may be made by molding, in a suitable machine, a mixture of the powdered compound moistened with an inert liquid diluent. Preferably, each tablet, cachet, caplet, or capsule contains from about 0.5 mg to about 500 mg of optically pure (−) norcisapride, more preferably from about 1 mg to about 350 mg, in combination with from about 1 mg to about 200 mg of a proton pump inhibitor or from about 1 mg to about 2400 mg of an $H_2$ receptor antagonist.

Pharmaceutical compositions of the present invention suitable for oral administration may be formulated as a pharmaceutical composition in a soft elastic gelatin capsule unit dosage form by using conventional methods well known in the art. See, e.g., Ebert, *Pharm. Tech,* 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols, such as polyethylene glycol and propylene glycol, triglycerides, surfactants, such as polysorbates, or a combination thereof.

In addition to the common dosage forms set out above, the compounds of the present invention may also be administered by controlled release means or delivery devices that are well known to those of ordinary skill in the art, such as those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are each incorporated herein by express reference thereto. These pharmaceutical compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, may be readily selected for use with the pharmaceutical compositions of the invention. Thus, single unit dosage forms suitable for oral administration, such as tablets, capsules, gelcaps, caplets, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of an active ingredient may be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, microspheres, or the like, or a combination thereof, that facilitates the controlled-release of the active ingredient.

Pharmaceutical compositions of the present invention may also be formulated for parenteral administration by injection (subcutaneous, bolus injection, intramuscular, or intravenous), and may be dispensed in a unit dosage form, such as a multidose container or an ampule. Such compositions for parenteral administration may be in the form of suspensions, solutions, emulsions, or the like in aqueous or oily vehicles, and in addition to the active ingredients may contain one or more formulary agents, such as dispersing agents, suspending agents, stabilizing agents, preservatives, and the like.

Another route of administration is transderrnal delivery, for example, via an abdominal skin patch.

The invention is further defined by reference to the following examples, describing in detail the preparation of the compound and the compositions of the present invention, as well as their utility. It will be apparent to those skilled in the art that many modifications, both to materials and methods, may be practiced without departing from the purpose and interest of this invention.

EXAMPLES

5.1 Example 1

Receptor Binding 5-$HT_3$ Receptor

Racemic norcisapride, racemic cisapride and their (−)- and (+)-stereoisomers were tested (Cerep, Celle l'Evescault, France) for binding to 5-$HT_3$ receptor subtypes derived from N1E-115 cells.

Following incubation with the appropriate ligands, the preparations were rapidly filtered under vacuum through GF/B glass fiber filters and washed with ice-cold buffer using a Brandel or Packard cell harvester. Bound radioactivity was determined with a liquid scintillation counter (LS 6000, Beckman) using a liquid scintillation cocktail (Formula 989).

Specific radioligand binding to the receptor was defined as the difference between total binding and nonspecific binding determined in the presence of an excess of unlabeled ligand. Results were expressed as a percent inhibition of specific binding obtained in the presence of the compounds. $IC_{50}$ were determined using concentrations ranging from $3 \times 10^{-10}$ M to $10^{-5}$ M to obtain full competition curves and were calculated by non-linear regression analysis. The results are shown in Tables 3 and 4 below.

Other active ingredients, such as granisetron, metoclopramide, ondansetron, renzapride, zacopride, tropisetron, and the like, can be tested using the methods described above.

5-HT$_4$ Receptor

Racemic norcisapride, racemic cisapride and their (−)- and (+)-stereoisomers were tested (Cerep, Celle l'Evescault, France) for binding to 5-HT$_4$ receptor subtypes derived from guinea-pig striata.

Following incubation with the appropriate ligands, the preparations were rapidly filtered under vacuum through GF/B glass fiber filters and washed with ice-cold buffer using a Brandel or Packard cell harvester. Bound radioactivity was determined with a liquid scintillation counter (LS 6000, Beckman) using a liquid scintillation cocktail (Formula 989).

Specific radioligand binding to the receptor was defined as the difference between total binding and nonspecific binding determined in the presence of an excess of unlabeled ligand. Results were expressed as a percent inhibition of specific binding obtained in the presence of the compounds. $IC_{50}$ were determined using concentrations ranging from $3 \times 10^{-10}$ M to $10^{-5}$ M to obtain full competition curves and were calculated by non-linear regression analysis. The results are shown in Tables 3 and 4 below.

Other active ingredients, such as cisapride and the like, can be tested using the methods described above.

TABLE 3

$IC_{50}$ (nM) Values for Binding to 5-HT$_3$ and 5-HT$_4$ Sites

| Compound | 5-HT$_3$ | 5-HT$_4$ | 5-HT$_3$/5-HT$_4$ Ratio |
|---|---|---|---|
| (±) Norcisapride | 8.2 | 686 | 0.012 |
| (+) Norcisapride | 4.5 | 331 | 0.014 |
| (−) Norcisapride | 30.4 | 1350 | 0.023 |

TABLE 4

$IC_{50}$ (nM) Values for Binding to 5-HT$_3$ and 5-HT$_4$ Sites

| Compound | 5-HT$_3$ | 5-HT$_4$ | 5-HT$_3$/5-HT$_4$ Ratio |
|---|---|---|---|
| (±) Cisapride | 365 | 169 | 2.2 |
| (+) Cisapride | 310 | 340 | 0.9 |
| (−) Cisapride | 2790 | 199 | 14.0 |

Agonist activity at 5-HT$_4$ receptor sites may also be assessed using an assay based on the ability of active compounds to increase cyclic AMP production in mouse embryo colloculi neurones grown in tissue culture (See Dumuis et al., *N. S. Arch. Pharmacol.*, 340:403–410 (1989)).

5.2 Example 2

Oral Formulation

Tablets

| | Quantity per Tablet in mg. | | |
|---|---|---|---|
| Formula | A | B | C |
| Active Ingredients: | | | |
| (−) Norcisapride | 5.0 | 10.0 | 25.0 |
| Lansoprazole | 5.0 | 15.0 | 30.0 |
| Lactose BP | 57.0 | 92.0 | 107.0 |
| Starch BP | 20.0 | 20.0 | 25.0 |
| Microcrystalline Cellulose | 10.0 | 10.0 | 10.0 |
| Hydrogenated Vegetable Oil | 1.5 | 1.5 | 1.5 |
| Polyvinylpyrrolidinone | 1.5 | 1.5 | 1.5 |
| Compression Weight | 100.0 | 150.0 | 200.0 |

The active ingredients, (−) norcisapride and lansoprazole, are sieved through a suitable sieve and blended with the lactose until a uniform blend is formed. Suitable volumes of water are added and the powders are granulated. After drying, the granules are then screened and blended with the remaining excipients. The resulting granules are then compressed into tablets of desired shape. Tablets of other strengths may be prepared by altering the ratio of active ingredient to the excipient(s) or the compression weight.

5.3 Example 3

Oral Formulation

Tablets

| | Quantity per Tablet in mg. | | |
|---|---|---|---|
| Formula | A | B | C |
| Active Ingredients: | | | |
| (−) Norcisapride | 5.0 | 10.0 | 25.0 |
| Famotidine | 10.0 | 20.0 | 40.0 |
| Lactose BP | 38.5 | 73.5 | 43.5 |
| Starch BP | 30.0 | 30.0 | 60.0 |
| Pregelatinized Maize Starch BP | 15.0 | 15.0 | 30.0 |
| Magnesium Stearate BP | 1.5 | 1.5 | 1.5 |
| Compression Weight | 100.0 | 150.0 | 540.0 |

The active ingredients, (−) norcisapride and famotidine, are sieved through a suitable sieve and blended with lactose, starch, and pregelatinized maize starch until a uniform blend is formed. Suitable volumes of water are added and the powders are granulated. After drying, the granules are then screened and blended with the remaining excipients. The resulting granules are then compressed into tablets of desired shape. Tablets of other strengths may be prepared by altering the ratio of active ingredient to the excipient(s) or the compression weight.

5.4 Example 4

Oral Formulation

Tablets

| Formula | Quantity per Tablet in mg. | | |
|---|---|---|---|
|  | A | B | C |
| Active Ingredient: (−) Norcisapride | 5.0 | 10.0 | 25.0 |
| Lactose BP | 48.5 | 43.5 | 78.5 |
| Starch BP | 30.0 | 30.0 | 30.0 |
| Pregelatinized Maize Starch BP | 15.0 | 15.0 | 15.0 |
| Magnesium Stearate BP | 1.5 | 1.5 | 1.5 |
| Compression Weight | 100.0 | 100.0 | 150.0 |

The active ingredient, (−) norcisapride, is sieved through a suitable sieve and blended with lactose, starch, and pregelatinized maize starch until a uniform blend is formed. Suitable volumes of water are added and the powders are granulated. After drying, the granules are then screened and blended with the remaining excipients. The resulting granules are then compressed into tablets of desired shape. Tablets of other strengths may be prepared by altering the ratio of active ingredient to the excipient(s) or the compression weight.

While the present invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating gastrointestinal disorders in a patient which comprises administering to said patient a therapeutically effective amount of (−) norcisapride, or a pharmaceutically acceptable salt thereof, substantially free of its (+) stereoisomer, and a therapeutically effective amount of at least one of a proton pump inhibitor, an $H_2$ receptor antagonist, or an optically pure stereoisomer or an active metabolite thereof, or a pharmaceutically acceptable salt thereof.

2. The method of claim 1, wherein the patient is a human.

3. The method of claim 1, wherein the gastrointestinal disorder is gastrointestinal motility dysfunction.

4. The method of claim 3, wherein the gastrointestinal motility dysfunction is selected from the group consisting of dyspepsia, gastroparesis, constipation, post-operative ileus, and intestinal pseudo obstruction.

5. The method of claim 1, wherein the gastrointestinal disorder is gastro-esophageal reflux disease, emesis, gastrointestinal ulcers, pathological hypersecretory condition, and gastric hyperacidity.

6. The method of claim 5, wherein the pathological hypersecretory condition is Zollinger-Ellison Syndrome.

7. The method of claim 5, wherein the gastric hyperacidity is selected from the group consisting of heartburn, acid indigestion, sour stomach, erosive esophagitis, and upset stomach.

8. The method of claim 1, wherein the amount of (−) norcisapride administered is from about 0.5 mg to about 500 mg.

9. The method of claim 8, wherein the amount of (−) norcisapride administered is from about 1 mg to about 350 mg.

10. The method of claim 1, wherein the proton pump inhibitor is administered and is selected from the group consisting of omeprazole, lansoprazole, rabeprazole, pantoprazole, hydroxy-omeprazole, desmethyl-pantoprazole, hydroxy-lansoprazole, and an optically pure stereoisomer thereof.

11. The method of claim 10, wherein the amount of proton pump inhibitor is from about 1 mg to about 200 mg.

12. The method of claim 11, wherein the amount of proton pump inhibitor is from about 5 mg to about 150 mg.

13. The method of claim 1, wherein the $H_2$ receptor antagonist is administered and is selected from the group consisting of cimetidine, ranitidine, famotidine, nizatidine, and an optically pure stereoisomer or an active metabolite thereof.

14. The method of claim 13, wherein the amount of $H_2$ receptor antagonist is from about 1 mg to about 2400 mg.

15. The method of claim 1, wherein at least one of (−) norcisapride and the proton pump inhibitor is administered orally.

16. The method of claim 15, wherein (−) norcisapride and the proton pump are orally administered as a tablet or a capsule.

17. The method of claim 1, wherein at least one of (−) norcisapride and the $H_2$ receptor antagonist is administered orally.

18. The method of claim 1, wherein the proton pump inhibitor or the $H_2$ receptor antagonist is administered together with (−) norcisapride parenterally, transdermally, rectally or sublingually.

19. The method of claim 1, which comprises administering either the proton pump inhibitor or $H_2$ receptor antagonist, and the (−) norcisapride, concurrently or sequentially.

20. A method of preventing or managing gastrointestinal disorders in a patient in need thereof, which comprises administering to said patient a therapeutically effective amount of (−) norcisapride, or a pharmaceutically acceptable salt thereof, substantially free of its (+) stereoisomer, and a therapeutically effective amount of at least one of a proton pump inhibitor, an $H_2$ receptor antagonist, or an optically pure stereoisomer or an active metabolite thereof, or a pharmaceutically acceptable salt thereof.

21. A pharmaceutical composition adapted for the treatment of a patient suffering from a gastrointestinal disorder which comprises a therapeutically effective amount of (−) norcisapride, or a pharmaceutically acceptable salt thereof, substantially free of its (+) stereoisomer; and a therapeutically effective amount of at least one of a proton pump inhibitor, $H_2$ receptor antagonist, or an optically pure stereoisomer or an active metabolite thereof, or a pharmaceutically acceptable salt thereof.

22. The pharmaceutical composition of claim 21, wherein the proton pump inhibitor is present and is selected from the group consisting of omeprazole, pantoprazole, rabeprazole, lansoprazole, hydroxy-omeprazole, hydroxy-lansoprazole, the carboxylic acid derivative of omeprazole, and desmethyl-pantoprazole.

23. The pharmaceutical composition of claim 21, wherein the $H_2$ receptor antagonist is present and is selected from the group consisting of cimetidine, ranitidine, famotidine, nizatidine, and N2-desmethylnizatidine.

* * * * *